United States Patent [19]

Richter

[11] B 4,014,755

[45] Mar. 29, 1977

[54] METHOD OF REFINING PYROMELLITIC ACID DIANHYDRIDE

[75] Inventor: Günther Richter, Eichenkamp, Germany

[73] Assignee: Veba-Chemie AG, Gelsenkirchen-Buer, Germany

[22] Filed: Feb. 11, 1974

[21] Appl. No.: 441,543

[44] Published under the second Trial Voluntary Protest Program on March 23, 1976 as document No. B 441,543.

[30] Foreign Application Priority Data

Feb. 16, 1973 Germany .................. 2307570

[52] U.S. Cl. .......................... 203/73; 260/346.3; 260/346.4
[51] Int. Cl.² ................................ C07D 307/89
[58] Field of Search ............... 260/346.3, 346.4; 203/73

[56] References Cited

FOREIGN PATENTS OR APPLICATIONS 45-4052   2/1970   Japan

OTHER PUBLICATIONS

Mazitov et al., Khim. Prom. (Moscow) 1969, Vol. 45(2), pp. 98–99, Chem. Abstracts (1969) Vol. 70, 106153.

Primary Examiner—Henry Jiles
Assistant Examiner—Bernard I. Dentz
Attorney, Agent, or Firm—Burgess, Dinklage & Sprung

[57] ABSTRACT

Process for purification of crude pyromellitic acid dianhydride produced by vapor phase oxidation of 1,2,4,5-tetraalkylbenzene with an oxygen-containing gas, having a purity of more than about 95% pyromellitic acid dianhydride. In a first distillation stage, said crude pyromellitic acid dianhydride is distilled at pressure of less than about 310 Torr, and temperature of less than about 350° C to distill overhead an impurities containing fraction amounting to less than about 20% of the crude introduced into the first stage, and provide a residue enriched in pyromellitic acid dianhydride. In a second distillation stage, the residue of the first stage is distilled at lower pressure and at temperature of less than about 325° C to distill overhead the purified pyromellitic acid dianhydride, and provide an impurities containing residue of less than about 12% of the crude introduced into the first step.

11 Claims, No Drawings

METHOD OF REFINING PYROMELLITIC ACID DIANHYDRIDE

BACKGROUND

Pyromellitic acid dianhydride (abbreviated hereinafter to PMDA) is an important starting product in the industry for the manufacture of special plastics. Polyimides or polyimide azopyrrolones prepared by the polycondensation of PMDA with aromatic diamines or tetramines have long been known as superior heat-resistant electrical insulating materials which are used in the form of castings, moldings, films and sheets and as coatings for electrical wires and cables. PMDA of high purity is required as the starting product for the preparation of these polyimides or polyimide azopyrrolones.

PMDA is prepared, for example, by catalytic gas phase oxidation of Durol (1,2,4,5-tetramethylbenzene) or other 1,2,4,5-tetraalkylbenzenes with gas containing oxygen, especially air, in the presence of catalysts. The impurities which PMDA made by this method generally contains are, for example, mono-, di-and tribasic acids or anhydrides, colored substances, etc.

In the state of the art there are a variety of processes for the refinement of crude PMDA prepared by gas phase oxidation of 1,2,4,5-tetramethylbenzene or other tetraalkylbenzenes. For instance, Belgian Pat. No. 676,048 proposes recrystallization from aromatic hydrocarbons with intermediate complexing, Netherlands Offenlegungsschrift No. 6,509,701 proposes recrystallization from dioxane or methyl isobutyl ketone, and U.S. Pat. No. 2,578,326 proposes vacuum sublimation from a suspension of the anhydride in inert, heat-resistant organic liquids. From Netherlands Offenlegungsschrift No. 6,516,840 it is furthermore in the prior art to perform the refinement by bubbling hot reaction gases through at elevated temperature. Also known is a process in which the vapor-gas mixture leaving the oxidation furnace is passed through water washers. In this manner the anhydrides are hydrated to the corresponding acid and the acid is dissolved. However, the impurities which develop during the oxidation also pass over into this solution. This is again followed by special refining processes requiring apparatus protected against corrosion. After the refinement the acid has to be dehydrated again, additional expensive operations being required for this purpose.

The known processes require large investments in apparatus and require large amounts of energy and time; furthermore, in some cases they deliver a very poor yield of pure product.

THE INVENTION

The invention is therefore addressed to the problem of creating a new process for the recovery of high purity PMDA, especially from PMDA obtained by the catalytic gas-phase oxidation of 1,2,4,5-tetramethylbenzene or other 1,2,4,5-tetraalkylbenzenes with oxygen-containing gas, in which the impurities comprising, e.g., mono-, di- and tribasic acids or anhydrides, colored substances, etc., are separated in a manner which is economically more advantageous than in processes of the prior art.

Pure PMDA has a melting point of about 287°C and a boiling point at atmospheric pressure of about 400°C. However, distillation, such as is commonly used in the preparation of phthalic acid anhydride, for example, has not been applicable as a refining process for PMDA prepared by catalytic gas phase oxidation from 1,2,4,5-tetraalkylbenzenes with oxygen-containing gases, because foreign substances contained in the PMDA decompose in the heat and thus form new impurities. Furthermore, naught but inadequate yields of distillate are obtained by this process. Even distillation at reduced pressure and at correspondingly low temperature does not bring satisfactory results because the decompositions take place even before or during the melting process. Furthermore, PMDA and its impurities sublimate heavily and this contaminates the distillate pathways, producing discoloration in the distillate. Even when a rectifying attachment is used, it is not possible, for these reasons, to arrive at a product of high purity. In practice, therefore, distillation or rectification processes have not achieved acceptance for the refinement of PMDA.

Surprisingly, it has now been found that PMDA, especially the raw product obtained by the catalytic gas phase oxidation of 1,2,4,5-tetraalkylbenzenes with oxygen-containing gases, may be purified by means of distillation if the raw product has a purity of more than 95%, preferably more than 98%. The purity can be 95 – 99.5%, preferably 98 – 99.5%. The distillation is performed under reduced pressure; in a first stage of the process, up to 20%, and preferably no more than 5%, for example 0.5 to 20%, preferably 1 to 5%, of the raw product is separated as first runnings at a pressure of less than about 310 Torr, especially 90 – 160 Torr, preferably 100 – 110 Torr, and at a temperature of less than 350°C, for example 290° to 350°C, preferably 300° to 320°C; and then in a second step at lower pressure, especially 70 – 120 Torr, preferably 90 – 100 Torr, and at less than 325°C, for example 290° to 325°C, preferably 300° to 310°C, the pyromellitic acid dianhydride distills over as the principal fraction except for a residue of less than about 12 wt-%, preferably less than about 6 wt-%, for example 0.5 to 12%, preferably 1 to 6%, with reference to the raw product put in. The percentage of "raw product" is the percentage of crude PMDA introduced into the first step.

In the refining of PMDA through distillation by the method of the invention, the impurities, which are separated in the first stage as a preliminary fraction, normally have a vapor pressure of approximately 70 Torr in the melting temperature range of raw PMDA, which is, for example, 276° to 287°C. Since a difference of at least 15°C is desirable between the boiling point and the solidification point of the material being distilled to assure proper operation, and on the other hand it is desirable to minimize temperature stress so as to protect the product, working pressures of around 100 Torr have proven to be good for the two distillations.

The two-step distillation may be performed batchwise in one apparatus or continuously in two stills in tandem. As a rule, a rectification attachment is not necessary, although with many input products rectification may bring an improvement in quality. Evaporation from a thin layer may be advantageous in the process of the invention, since it results in the production of less residue.

The PMDA to be used in the distillation may be obtained by one of the above-mentioned refinement processes from the raw products produced in the catalytic gas phase oxidation; it is better, however, to use a raw product which, being produced by a suitable oxidation and deposition method, will have sufficient purity.

An excellent method of obtaining crude PMDA which is the feed to the purification process of the invention is fractional desublimation in accordance with the method described in Austrian Pat. Nos. 290,509 and 298,471. This method makes it possible to eliminate irregularities, such as insufficient selectivity of the catalyst or erroneous operating conditions in the oxidation stage which do not produce a distillable raw PMDA. Furthermore, the more easily boiling impurities which lead to the above-described decompositions before and during the melting are not contained in fractionally desublimated PMDA.

Thus, the invention provides a process for purification of crude pyromellitic acid dianhydride produced by vapor phase oxidation of 1,2,4,5-tetraalkylbenzene with an oxygen-containing gas, having a purity of more than about 95% pyromellitic acid dianhydride. The process includes two steps. In the first step, said crude pyromellitic acid dianhydride is distilled at pressure of less than about 310 Torr, and temperature of less than about 350°C to distill overhead an impurities-containing fraction amounting to less than about 20% of the crude introduced into this first step, and provide a residue enriched in pyromellitic acid dianhydride. In the second step, the residue of the first step is distilled at lower pressure than is used in the first step, and at temperature of less than about 325°C to distill overhead the purified pyromellitic acid dianhydride and provide an impurities-containing residue of less than about 12% of the crude introduced into the first step.

EXAMPLE

Technical 5-isopropyl pseudocumene was oxidized with air in a tubular solid-bed catalyst furnace of conventional construction, at a charging rate of about 16 grams of the pseudocumene per normal cubic meter of air. The catalyst was a mixture of 75% $V_2O_5$ and 25% $TiO_2$ on a carrier of silicium carbide as described in German Auslegeschrift No. 1246707. thus obtained was fractionally desublimated at temperatures between 250° and 130°C by the method described in Austrian Pat. No. 290,509. A white to light gray product was thus obtained which contained 99.1% PMDA and had an acid number of 1010 (theory: 1028). The resulting crude PMDA was purified in a batch process according to the invention, as follows.

This crude PMDA was passed through a falling film evaporator operated at a pressure of 110 Torr, and a temperature of 312°C, 2% of the input PMDA being removed in the form of a yellowish distillate.

Then the effluent was again subjected to distillation in another falling film evaporator the vapor temperature being 308°C and the pressure in the evaporator amounting to 100 Torr, whereupon the main fraction distilled over except for a dark brown residue, still capable of flow, amounting to 3% of the crude PMDA introduced into the first step. The PMDA obtained was of pure white color; its acid number was 1028. No impurities could be detected by the known methods of analysis.

If, however, the PMDA was obtained from the gases leaving the oxidation furnace by mere desublimation, it had a purity of 94% PMDA and an acid number of 965; its color was gray. The product could be distilled; however, in spite of the loss of 20% first runnings in the first step and a residue of 13% in the second step, it was not possible, even by repeating the evaporation twice, to obtain a PMDA of sufficient purity.

In a third experiment the PMDA was obtained from the gases leaving the oxidation furnace by means of a cooling trap. The product had a purity of 89% PMDA and an acid number of 915; its color was dark gray. This product could not be distilled; it decomposed largely even before the melting temperature was reached.

The catalyst used in the oxidation can be any of the conventional catalysts known for the oxidation.

The purity of the residue enriched in PMDA, produced in the first distillation step, can be more than 95%, preferable more than 98% PMDA.

The purity of the product of the second distillation step is 99.5%, preferable 99.9 %, up to pure PMDA as is produced in the example.

For the purposes of this specification, purity can be determined by gas chromatography and acid number by titration.

By "Torr" is meant mm of mercury.

Herein, % is in wt.% unless otherwise indicated.

What is claimed is:

1. Process for purification of crude pyromellitic acid dianhydride produced by vapor oxidation of 1,2,4,5-tetraalkylbenzene with an oxygen containing gas, having a purity of more than about 95% pyromellitic acid dianhydride, which comprises the following steps:
    a. distilling said crude pyromellitic acid dianhydride at pressure of about 90–160 Torr, and temperature of about 290°–350°C to distill overhead an impurities-containing fraction amounting to less than about 20% of the crude introduced into step (a), and provide a residue enriched in pyromellitic acid dianhydride,
    b. distilling the residue of step (a) at lower pressure which is 70 – 120 Torr and at temperature of about 290°–325°C to distill overhead the purified pyromellitic acid dianhydride, and provide and impurities-containing residue of less than about 12% of the crude introduced into step (a).

2. Process according to claim 1, the crude pyromellitic acid dianhydride introduced into step (a) having a purity of more than about 98%.

3. Process according to claim 1, the impurities-containing fraction distilled overhead in step (a) being less than about 5% of the crude introduced into step (a).

4. Process according to claim 1, the impurities-containing residue produced in step (b) being less than about 6% of the crude introduced into step (a).

5. Process according to claim 1, the crude pyromellitic acid dianhydride introduced into step (a) having a purity of more than about 98%, the impurities-containing fraction distilled overhead in step (a) being less than about 5% of the crude introduced into step (a), the impurities-containing residue produced in step (b) being less than about 6% of the crude introduced into step (a).

6. Process according to claim 1, said vapor phase oxidation being a catalytic vapor phase oxidation.

7. Process according to claim 1, wherein said crude pyromellitic acid dianhydride is the product of vapor phase oxidation of 1,2,4,5-tetraalkylbenzene with an oxygen-containing gas, which is subjected to purification to provide the crude having a purity of more than about 95%.

8. Process according to claim 1, wherein the pressure in step (a) is about 100–110 Torr, and the pressure in step (b) is about 90–100 Torr.

9. Process according to claim 1, wherein the distillation step (b) is a batch distillation.

10. Process according to claim 1, wherein in Step (a) the pressure is 100–110 Torr and the temperature is 300°–320°C, and in Step (b), the pressure is 90–100 Torr and the temperature is 300–310.

11. Process according to claim 1, wherein the residue of Step (a) is more than 98% pyromellitic acid dianhydride, and the purified pyromellitic acid dianhydride produced in Step (b) is at least 99.9%.

* * * * *

UNITED STATES PATENT AND TRADEMARK OFFICE
CERTIFICATE OF CORRECTION

PATENT NO. : 4,014,755
DATED : March 29, 1977
INVENTOR(S) : Günther Richter

It is certified that error appears in the above-identified patent and that said Letters Patent are hereby corrected as shown below:

Column 4, line 37, change "and" (second occurrence) to --an--.

Signed and Sealed this

First Day of November 1977

[SEAL]

Attest:

RUTH C. MASON
*Attesting Officer*

LUTRELLE F. PARKER
*Acting Commissioner of Patents and Trademarks*